United States Patent [19]

Nagamine et al.

[11] Patent Number: 5,045,562

[45] Date of Patent: Sep. 3, 1991

[54] 1,3,5-TRITHIANE DERIVATIVES AND PHARMACEUTICAL COMPOSITIONS THEREOF

[75] Inventors: Masashi Nagamine, Nishinomiya; Kunikazu Hiraga, Osaka; Atsushi Sakai; Matazaemon Uchida, both of Kawachinagano, all of Japan

[73] Assignee: Nihon Nohyaku Co., Ltd., Tokyo, Japan

[21] Appl. No.: 258,667

[22] Filed: Oct. 17, 1988

Related U.S. Application Data

[62] Division of Ser. No. 73,449, Jul. 14, 1987, Pat. No. 4,816,475.

[30] Foreign Application Priority Data

Jul. 15, 1986 [JP] Japan .................. 61-166167

[51] Int. Cl.$^5$ .................. A61K 31/385; C07D 341/00
[52] U.S. Cl. ...................................... 514/435; 549/19
[58] Field of Search ........................ 549/19; 514/435

[56] References Cited

U.S. PATENT DOCUMENTS

| | | | |
|---|---|---|---|
| 3,525,751 | 8/1970 | Fried | 549/19 |
| 3,792,043 | 2/1974 | Chang | 540/70 |

FOREIGN PATENT DOCUMENTS

| | | |
|---|---|---|
| 1643492 | 3/1972 | Fed. Rep. of Germany . |
| 61408 | 3/1982 | France . |
| 57-48980 | of 1982 | Japan . |
| 98657 | 8/1978 | Poland . |

OTHER PUBLICATIONS

European Search Report, Appln. No. 87110180.4-2110, Feb. 2, 1990.
Chemical Abstracts, C. Paul Bianchi, 1-Pharmacodynamics, Jun. 19, 1978.
Chemical Abstracts, C. Paul Bianchi, 1-Pharmacology, Apr. 26, 1982.
M. Mikoxajczyk et al., A New General Synthesis of Ketene Thioacetals, Tetrahydro Letters-No. 31, pp. 2731-2734, 1976.
Mikolajczyk et al., *Tetrahedron* (34), pp. 3081-3088 (1978).

*Primary Examiner*—Mary C. Lee
*Assistant Examiner*—Jacqueline Haley
*Attorney, Agent, or Firm*—Cushman, Darby & Cushman

[57] ABSTRACT

1,3,5-trithiane derivatives represented by the formula (I)

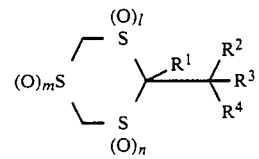

wherein the substituents are defined herein, are disclosed. The trithiane derivatives and their compositions are useful as anti-arteriosclerotic or anti-hyperlipemic agents.

18 Claims, No Drawings

1,3,5-TRITHIANE DERIVATIVES AND PHARMACEUTICAL COMPOSITIONS THEREOF

This is a division of application Ser. No. 07/073,449, filed July 14, 1987, now U.S. Pat. No. 4,816,475.

FIELD OF THE INVENTION AND RELATED ART STATEMENTS

1. Field of the Invention

This invention relates to a 1,3,5-trithiane derivative represented by the general formula (I):

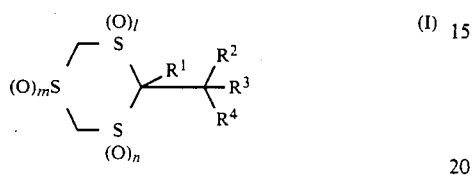

(wherein $R^1$ is a hydrogen atom, $R^2$ is a hydrogen atom, a hydroxyl group or an imidazolyl group, or $R^{2,}$ when taken together with $R^{1,}$ forms a double bond between the carbon atom of the trithiane ring and the one to which $R^3$ and $R^4$ are bonded, $R^3$ is a hydrogen atom; an unsubstitutedphenyl group; a substituted-phenyl group having one or two substituents selected from the group consisting of halogen atoms, $C_1$- to $C_5$-alkyl groups, $C_1$- to $C_5$-haloalkyl groups $C_3$- to $C_7$-cycloalkyl groups, a hydroxyl group, $C_1$- to $C_5$-alkoxy groups (whose alkyl portion is optionally substituted by a morpholino group, an N-substituted-piperizino group having a $C_1$- to $C_3$-alkyl group as the substitutent, a $C_3$- to $C_{10}$-alkoxycarbonyl group, a phenyl group or a halophenyl group), $C_3$- to $C_7$-cycloalkoxy groups, phenoxy group (whose phenyl portion is optionally substituted by a halogen atom, a $C_1$- to $C_5$-alkyl group or a $C_1$- to $C_5$-alkoxy group), phenylthio group, phenylsulfinyl group, nitro group, N,N-$C_2$- to $C_8$-dialkylamino groups, morpholino group, imidazolyl group, phenyl group, halophenyl groups, phenylalkyl groups and pyridyl group; a heteroaromatic group; a polycyclic fused ring group; a substituted-$C_1$- to $C_5$-alkyl group having a phthalimido-1-yl group or a phenoxyphenyl group as the substituent; or a halostyryl group, or $R^{3,}$ when taken together with $R^{2,}$ forms a $C_1$- to $C_9$-alkylidene group, $R^4$ is a hydrogen atom; a $C_1$- to $C_8$-alkyl group (which is optionally substituted by a halogen atom, a $C_2$- to $C_5$-alkoxycarbonyl group, a hydroxycarbonyl group, hydroxy or a $C_1$- to $C_5$-alkoxy group); a $C_{15}$- to $C_{20}$-alkenylene group; an unsubstituted-phenyl group; a substituted-phenyl group having one or two substituents selected from the group consisting of halogen atoms, $C_1$- to $C_6$-alkyl groups, $C_1$- to $C_4$-haloalkyl groups, $C_1$- to $C_5$-alkylthio groups, $C_2$- to $C_6$-alkoxycarbonyl groups and hydroxycarbonyl group; or a halostyryl group, or $R^3$ and $R^{4,}$ when taken together with the carbon atom to which they are bonded, represent a fluoren-9-ylidene group, each of l, m and n is zero or an integer of 1 or 2, and $R^4$ is a group other than phenyl group in the case where $R^3$ is a phenyl group), and an anti-arteriosclerotic or anti-hyperlipemic agent containing said derivative as active ingredient.

2. Related Art Statement

As compounds akin to the compounds of the general formula [I], there are known Compound A [Tetrahedron Letter 31, 2731-2734 (1976)] and Compound B [the specification of U.S. Patent 3,525,751]:

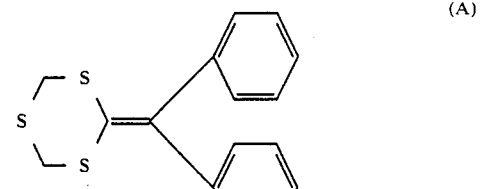

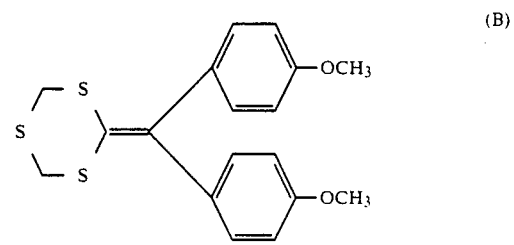

but as to their uses, it is only known that Compound B has follicle hormone activity.

OBJECT AND SUMMARY OF THE INVENTION

As a result of extensive study, the present inventors found that the trithiane derivatives of the general formula (I) had a cholesterol-reducing effect and an antihyperlipemic activity and were useful as antiarteriosclerotic agents and anti-hyperlipemic agents.

An object of the present invention is to provide a novel trithiane derivative having a pharamocological activity.

Another object of the present invention is to provide a pharmaceutical composition useful as an antiarteriosclerosis and the like.

Further another object of the present invention is to provide a method of preparing said trithiane derivative.

DETAILED DESCRIPTION OF PREFERRED EMBODIMENT

The compound of the general formula (I) can be produced by the following process:

Process A:

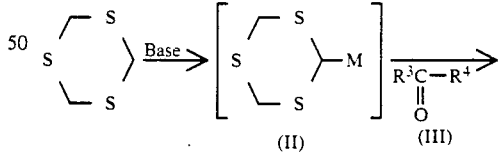

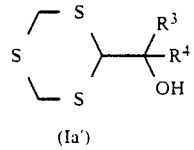

wherein $R^3$ and $R^4$ have the same meanings as defined above, and M is an alkali metal atom.

In detail, a compound of the general formula (Ia') can be obtained by allowing a base to act on 1,3,5-trithiane in an anhydrous inert solvent to convert 1,3,5-trithiane into an alkaline metal salt thereof (II), and then slowly dropping thereto a solution prepared by dissolving a compound of the general formula (III) in an anhydrous inert solvent.

As the solvents usable in these reactions, aprotic aqueous inert solvents are preferred, and there can be exemplified, for example, hydrocarbons such as n-hexane, cyclohexane, isooctane, benzene and the like; and ethers such as diethyl ether, dioxane, tetrahydrofuran, dimethoxyethane and the like.

The base includes n-butyl lithium, sec-butyl lithium, tert-butyl lithium, phenyl lithium, lithium diisopropylamide, lithium dicyclohexylamide, lithium hexamethyldisilazide, sodium hydride, potassium hydride, etc.

The using amount of the base is equimolar with 1,3,5-trithiane. The reaction temperature is selected in the range of $-78°$ C. to $50°$ C., preferably $-78°$ C. to $20°$ C. Although the reaction time is varied depending on the respective reaction temperature and reaction scale, it may be selected in the range of 30 minutes to 48 hours.

In carrying out the reactions, the reactants for each reaction are used in equimolar amount because the reaction is an equimolar reaction, though either of them may be used in excess.

Process B:

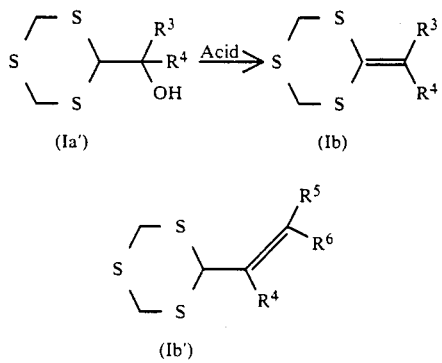

wherein $R^4$ has the same meanings as defined above, and $R^5$ and $R^6$ are a hydrogen atom or $C_1$- to $C_5$-alkyl group.

A compound of the general formula (Ib) can be obtained by dehydrating a compound of the general formula (Ia') by use of an acid in an inert solvent. The dehydration yields a compound of the general formula (Ib') in some cases depending on the kind of $R^3$.

As the solvent usable in the present reaction, any solvent may be used so long as it does not inhibit the reaction, and there can be exemplified hydrocarbons such as benzene, toluene, chlorobenzene and the like; halogenated hydrocarbons such as dichloromethane, chloroform and the like; ethers such as dioxane, tetrahydrofuran and the like; and esters such as ethyl acetate and the like.

The acid includes, for example, p-toluenesulfonic acid, methanesulfonic acid, camphorsulfonic acid, and trifluoroacetic acid. The using amount of the acid is a catalytic amount with regard to the compound of the general formula (Ia').

The reaction temperature is selected in the range of room temperature to the boiling point of the solvent. Although the reaction time is varied depending on the reaction temperature and the reaction scale, it is selected in the range of 5 minutes to 24 hours.

Process C:

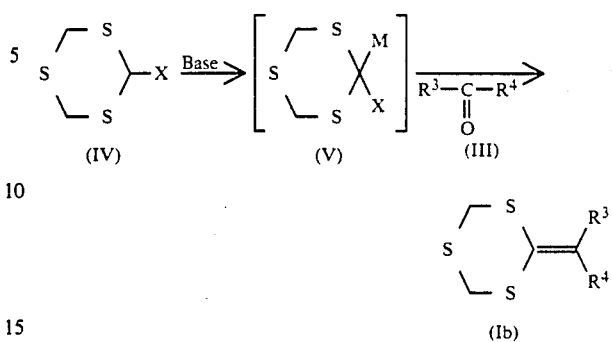

wherein $R^3$, $R^4$ and M have the same meanings as defined above, and X is a trimethylsilyl group, a triphenylsilyl group, a dialkylphosphoryl group, a tributylstannyl group, or a chlorotriphenylphophonium group.

In detail, a compound of the general formula (Ib) can be obtained by allowing a base to act on a compound of the general formula (IV) in an anhydrous inert solvent to convert this compound into an alkali metal salt thereof (V), and then slowly dropping thereto a solution prepared by dissolving a compound of the general formula (III) in an inert solvent.

As the solvent usable in each of these reactions, any solvent may be used so long as it does not inhibit the reaction, and for example, those used in Process A can be exemplified. As the base, those used in Process A can be exemplified.

The reaction temperature is selected in the range of $-78°$ C. to $50°$ C., preferably $-78°$ C. to $20°$ C. Although the reaction time is varied depending on the respective reaction temperature and reaction scale, it may be selected in the range of 30 minutes to 48 hours.

In carrying out the reactions, the reactants for each reaction are used in equimolar amount because the reaction is an equimolar reaction, though either of them may be used in excess.

Process D:

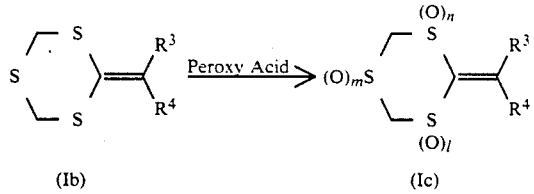

wherein $R^3$ and $R^4$ have the same meanings as defined above, and each of l, m and n is zero, 1 or 2.

In detail, a compound of the general formula (Ic) can be obtained by reacting a compound of the general formula (Ib) with a peroxy acid in an inert solvent.

As the solvent used in this reaction, any solvent may be used so long as it does not inhibit the reaction, and there can be exemplified, for example, halogenated hydrocarbons such as dichloromethane, chloroform and the like; hydrocarbons such as benzene, toluene, chlorobenzene and the like; and esters such as acetic acid esters and the like.

The peroxy acid includes aqueous hydrogen peroxide solution, m-chloroperbenzoic acid, peracetic acid, trifluoroperacetic acid, t-butylhydroperoxide, etc.

The reaction temperature is selected in the range of −98° C. to room temperature. The reaction time may be selected in the range of 1 to 48 hours depending on the reaction temperature and the reaction scale.

In carrying out the reaction, the peroxy acid is used preferably in an amount of 1 to 3 times the number of moles of the compound of the general formula (Ib) depending on the purposes because this compound contains 3 sulfur atoms to be oxidized.

Process E:

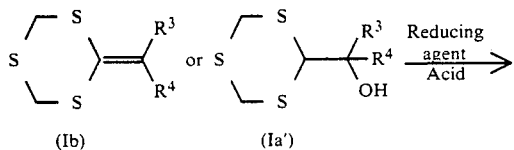

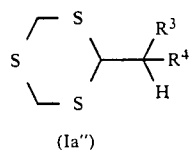

wherein $R^3$ and $R^4$ have the same meanings as defined above.

In detail, a compound of the general formula (Ia″) can be obtained by reacting a compound of the general formula (Ia′) or (Ib) by use of a reducing agent in the presence of an acid in an inert solvent.

As the solvent used in this reaction, any solvent may a used so long as it does not inhibit the reaction, and for example, those used in Process A can be exemplified.

The acid includes titanium tetrachloride, diethyl etherate of boron trifluoride, trifluoroacetic acid, etc.

The reducing agent includes, for example, trimethylsilane and triethylsilane.

The reaction temperature is preferably 0° C. to room temperature because when it is high, dehydration reaction also occurs. The reaction time is selected in the range of 1 to 24 hours depending on the reaction temperature and the reaction scale.

In carrying out the reaction, the reducing agent and the acid are used preferably in amounts equimolar with the compound of the general formula (Ia′) or (Ib) or in larger amounts.

Process F:

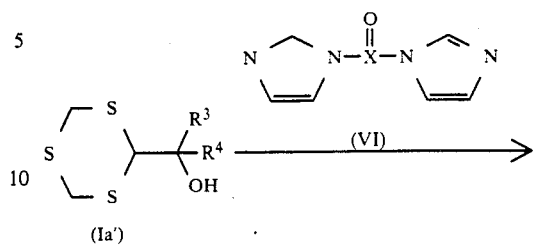

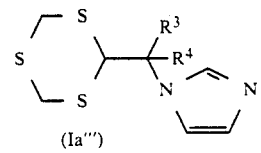

wherein $R^3$ and $R^4$ have the same meanings as defined above, and X is a carbon atom or a sulfur atom.

In detail, a compound of the general formula (Ia‴) can be obtained by reacting a compound of the general formula (Ia′) with a compound of the general formula VI in an inert solvent.

As the solvent used in the reaction, any solvent may be used so long as it does not inhibit the reaction, and there can be exemplified, for example, halogenated hydrocarbons such as dichloromethane, chloroform and the like; and aromatic hydrocarbons such as benzene, toluene, chlorobenzene and the like.

The reaction temperature is selected in the range of 0° C. to the boiling point of the solvent. The reaction time is selected in the range of 1 minute to 48 hours depending on the reaction temperature and the reaction scale.

In carrying the reaction, although the theoretical amount of compound of the general formula VI is ½ mole per mole of the compound of the general formula (Ia′), employment of either of these compounds in excess causes no trouble in the reaction.

The deserired compounds obtained by Processes A to G can be separated by a conventional method and purified by a method such as recrystallization, column chromatography, etc.

Next, typical examples of the compound of the general formula (I) are listed in Tables Ia to Ic, but this invention is not limited thereto.

General formula (I):

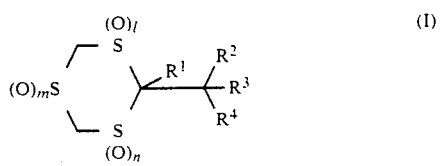

TABLE I-a

In general formula (Ia):

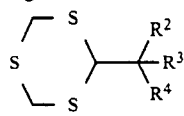

| Compound No. | $R^2$ | $R^3$ | $R^4$ | Physical properties (melting point or refractive index) |
|---|---|---|---|---|
| 1 | OH | 2,4-dichlorophenyl | phenyl | m.p. 133.0–133.5° C. |
| 2 | OH | 4-isopropylphenyl | phenyl | m.p. 134.0–135.0° C. |
| 3 | OH | 4-tert-butylphenyl | phenyl | m.p. 139.0–140.5° C. |
| 4 | OH | 4-morpholinophenyl | phenyl | m.p. 172.0–173.0° C. |
| 5 | OH | 4-fluorophenyl | 2-fluorophenyl | m.p. 133.0–134.5° C. |
| 6 | H | 4-fluorophenyl | 4-fluorophenyl | m.p. 170.0–171.0° C. |
| 7 | OH | 4-fluorophenyl | 4-fluorophenyl | m.p. 124.0–125.0° C. |
| 8 | 1-imidazolyl | 4-fluorophenyl | 4-fluorophenyl | m.p. 93.5–96.0° C. |
| 9 | OH | 4-fluorophenyl | 2,4-dichlorophenyl | m.p. 132.5–133.5° C. |
| 10 | OH | 4-methylphenyl | 4-fluorophenyl | m.p. 116.0–118.0° C. |
| 11 | OH | 4-chlorophenyl | 2-chlorophenyl | m.p. 162.0–163.0° C. |

TABLE I-a-continued

In general formula (Ia):

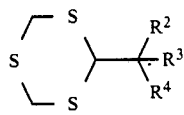

| Compound No. | R² | R³ | R⁴ | Physical properties (melting point or refractive index) |
|---|---|---|---|---|
| 12 | OH | —C₆H₄—Cl (p) | —C₆H₄—Cl (p) | m.p. 145.0–147.0° C. |
| 13 | OH | 3,5-dimethylisoxazol-4-yl | —C₆H₄—F (p) | m.p. 150.5–151.5° C. |
| 14 | OH | 3,5-dimethylisoxazol-4-yl | —C₆H₄—CH₃ (p) | m.p. 180.0–180.5° C. |
| 15 | OH | —C₆H₅ | C₃H₇-i | m.p. 93.5–95.0° C. |
| 16 | H | —C₆H₄—O—C₆H₅ (p) | C₂H₅ | Paste |
| 17 | OH | —C₆H₄—O—C₆H₅ (p) | CH₃ | m.p. 70.0–71.0° C. |
| 18 | OH | —C₆H₄—O—C₆H₅ (p) | C₂H₅ | $n_D^{18.5}$ 1.6204 |
| 19 | =C(CH₃)₂ | | —C₆H₄—F (p) | Paste |

TABLE 1-b

In the general formula (Ib):

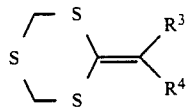

| Compound No. | R³ | R⁴ | Physical properties (melting point or refractive index) |
|---|---|---|---|
| 20 | —C₆H₄—F (p) | —C₆H₅ | m.p. 148.0–149.0° C. |

TABLE 1-b-continued
In the general formula (Ib):
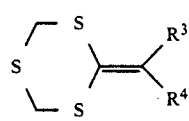
| Compound No. | R³ | R⁴ | Physical properties (melting point or refractive index) |
|---|---|---|---|
| 21 | 3-Cl-C₆H₄ | C₆H₅ | m.p. 119.0–120.0° C. |
| 22 | 4-Cl-C₆H₄ | C₆H₅ | m.p. 157.0–157.5° C. |
| 23 | 3,4-Cl₂-C₆H₃ | C₆H₅ | m.p. 86.0–88.0° C. |
| 24 | 4-CH₃-C₆H₄ | C₆H₅ | m.p. 159.0–160.0° C. |
| 25 | 4-i-C₃H₇-C₆H₄ | C₆H₅ | m.p. 113.0–115.0° C. |
| 26 | 4-t-C₄H₉-C₆H₄ | C₆H₅ | m.p. 133.0–134.0° C. |
| 27 | 4-CF₃-C₆H₄ | C₆H₅ | m.p. 144.0–145.0° C. |
| 28 | 4-OCH₃-C₆H₄ | C₆H₅ | m.p. 151.0–152.0° C. |
| 29 | 4-OH-C₆H₄ | C₆H₅ | m.p. 175.0–175.5° C. |
| 30 | 4-(morpholino)-C₆H₄ | C₆H₅ | m.p. 203.0–205.0° C. |
| 31 | 4-F-C₆H₄ | 3-F-C₆H₄ | m.p. 103.0–104.0° C. |

TABLE 1-b-continued
In the general formula (Ib):
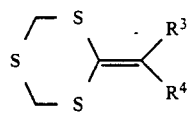
| Compound No. | R³ | R⁴ | Physical properties (melting point or refractive index) |
|---|---|---|---|
| 32 | 4-F-phenyl | 3-F-phenyl | m.p. 87.0–88.0° C. |
| 33 | 4-F-phenyl | 4-F-phenyl | m.p. 153.0–153.5° C. |
| 34 | 4-F-phenyl | 2,4-diF-phenyl | m.p. 125.0–127.0° C. |
| 35 | 4-F-phenyl | 4-Cl-phenyl | m.p. 150.0–150.5° C. |
| 36 | 4-F-phenyl | 3,4-diCl-phenyl | m.p. 107.0–108.0° C. |
| 37 | 4-F-phenyl | 4-CF₃-phenyl | m.p. 179.0–180.0° C. |
| 38 | 4-F-phenyl | 4-CH₃-phenyl | m.p. 170.0–171.5° C. |
| 39 | 4-F-phenyl | 4-SCH₃-phenyl | m.p. 156.5–157.0° C. |
| 40 | 4-F-phenyl | 4-CO₂CH₃-phenyl | m.p. 176.0–180.0° C. |
| 41 | 4-F-phenyl | 4-CO₂H-phenyl | m.p. >280° C. |

TABLE 1-b-continued
In the general formula (Ib):
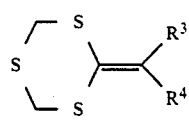
| Compound No. | $R^3$ | $R^4$ | Physical properties (melting point or refractive index) |
|---|---|---|---|
| 42 | 4-Cl-C₆H₄ | 2-Cl-C₆H₄ | m.p. 96.0–97.5° C. |
| 43 | 4-Cl-C₆H₄ | 3-Cl-C₆H₄ | m.p. 109.0–110.5° C. |
| 44 | 4-Cl-C₆H₄ | 4-Cl-C₆H₄ | m.p. 160.0–160.5° C. |
| 45 | 4-Br-C₆H₄ | 4-Br-C₆H₄ | m.p. 203.0–204.0° C. |
| 46 | 4-CH₃-C₆H₄ | 4-CH₃-C₆H₄ | m.p. 159.5–160.0° C. |
| 47 | 4-CH₃-C₆H₄ | 4-(t-C₄H₉)-C₆H₄ | m.p. 145.0–146.0° C. |
| 48 | C₆H₅ | CH₃ | $n_D^{23.5}$ 1.6898 |
| 49 | C₆H₅ | CF₃ | m.p. 81.0–82.0° C. |
| 50 | 4-F-C₆H₄ | H | $n_D^{24.0}$ 1.6889 |
| 51 | 4-F-C₆H₄ | CH₃ | m.p. 57.0–58.0° C. |
| 52 | 4-F-C₆H₄ | C₂H₅ | m.p. 81.0° C. |

TABLE 1-b-continued
In the general formula (Ib):
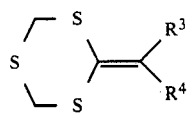
| Compound No. | $R^3$ | $R^4$ | Physical properties (melting point or refractive index) |
|---|---|---|---|
| 53 | 4-F-C6H4- | $C_3H_7$-n | m.p. 84.0–85.0° C. |
| 54 | 4-F-C6H4- | $C_5H_{11}$-n | m.p. 69.0° C. |
| 55 | 4-Cl-C6H4- | $CH_3$ | m.p. 81.5–83.0° C. |
| 56 | 4-Br-C6H4- | $CH_3$ | m.p. 102.0–102.5° C. |
| 57 | 2-CH3-C6H4- | $CH_3$ | m.p. 80.5–82.0° C. |
| 58 | 3-CH3-C6H4- | $CH_3$ | m.p. 42.0–44.5° C. |
| 59 | 4-CH3-C6H4- | $CH_3$ | m.p. 82.5–83.0° C. |
| 60 | 4-cyclohexyl-C6H4- | $CH_3$ | m.p. 107.0–109.0° C. |
| 61 | 4-phenyl-C6H4- | $CH_3$ | m.p. 99.0–100.0° C. |
| 62 | 4-(4-Br-C6H4)-C6H4- | $CH_3$ | m.p. 153.5–154.5° C. |
| 63 | 4-benzyl-C6H4- | $CH_3$ | m.p. 48.0–50.0° C. |

TABLE 1-b-continued
In the general formula (Ib):
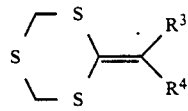
| Compound No. | $R^3$ | $R^4$ | Physical properties (melting point or refractive index) |
|---|---|---|---|
| 64 | -C6H4-N(CH3)2 (p) | CH3 | m.p. 109.0–110.5° C. |
| 65 | -C6H4-morpholino (p) | CH3 | m.p. 114.0–115.0° C. |
| 66 | -C6H4-imidazol-1-yl (p) | CH3 | m.p. 123.0–125.5° C. |
| 67 | -C6H4-S-C6H5 (p) | CH3 | m.p. 49.5–51.5° C. |
| 68 | -C6H4-S(O)-C6H5 | CH3 | m.p. 97.0–97.5° C. |
| 69 | -C6H4-NO2 (p) | CH3 | m.p. 110.0–112.0° C. |
| 70 | -C6H5 | COOC2H5 | m.p. 102.5–103.5° C. |
| 71 | -C6H4-Cl (p) | COOC2H5 | m.p. 122.5–125.0° C. |
| 72 | -C6H4-Cl (p) | COOH | m.p. 185.0–186.0° C. |
| 73 | -C6H5 | —(CH2)6(CH2CH=)2—(CH2)4CH3 (cis form) | $n_D^{18.5}$ 1.5709 |
| 74 | -C6H4-OH (p) | CH3 | m.p. 175.0–175.5° C. |

TABLE 1-b-continued

In the general formula (Ib):

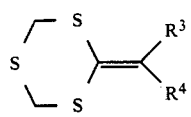

| Compound No. | R³ | R⁴ | Physical properties (melting point or refractive index) |
|---|---|---|---|
| 75 | —⟨C₆H₄⟩—OCH₃ (para) | CH₃ | m.p. 95.0–96.5° C. |
| 76 | —⟨C₆H₄⟩—OC₃H₇-i (para) | CH₃ | m.p. 63.5–64.5° C. |
| 77 | —⟨C₆H₃⟩(OCH₃)(OCH₃) | CH₃ | m.p. 104.0–104.5° C. |
| 78 | —⟨C₆H₄⟩—OC₅H₁₁-n (para) | CH₃ | m.p. 59.0–60.5° C. |
| 79 | —⟨C₆H₄⟩—O—cyclohexyl (para) | CH₃ | m.p. 70.0–71.0° C. |
| 80 | —⟨C₆H₄⟩—O(CH₂)₃N(morpholino) (para) | CH₃ | m.p. 95.0–98.0° C. |
| 81 | —⟨C₆H₄⟩—O(CH₂)₃N(piperazino)NCH₃ (para) | CH₃ | m.p. 73.0–74.0° C. |
| 82 | —⟨C₆H₄⟩—OC(CH₃)₂COOC₂H₅ (para) | CH₃ | $n_D^{18.5}$ 1.6061 |
| 83 | —⟨C₆H₄⟩—OCH₂—⟨C₆H₅⟩ (para) | CH₃ | m.p. 97.0–98.0° C. |
| 84 | —⟨C₆H₄⟩—OCH₂—⟨C₆H₄⟩—Cl (para) | CH₃ | m.p. 111.0–112.0° C. |
| 85 | —⟨C₆H₄⟩—CH₃ (para) | —CH₂CH₂COOCH₃ | m.p. 96.0–97.0° C. |

TABLE 1-b-continued

In the general formula (Ib):

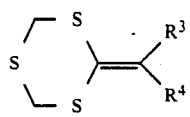

| Compound No. | R³ | R⁴ | Physical properties (melting point or refractive index) |
|---|---|---|---|
| 86 | 4-phenoxyphenyl | H | m.p. 69.5–72.5° C. |
| 87 | 3-phenoxyphenyl | CH₃ | Paste |
| 88 | 4-phenoxyphenyl | CH₃ | m.p. 90.0–90.5° C. |
| 89 | 4-phenoxyphenyl | C₂H₅ | m.p. 57.0–58.0° C. |
| 90 | 4-phenoxyphenyl | C₃H₇-n | m.p. 48.0–51.0° C. |
| 91 | 3-phenoxyphenyl | C₄H₉-n | Paste |
| 92 | 4-phenoxyphenyl | C₄H₉-n | $n_D^{23.5}$ 1.6445 |
| 93 | 4-phenoxyphenyl | C₄H₉-i | $n_D^{23.0}$ 1.6488 |
| 94 | 4-phenoxyphenyl | C₅H₁₁-n | m.p. 57.0–59.0° C. |
| 95 | 4-phenoxyphenyl | CF₃ | m.p. 81.0–83.0° C. |

TABLE 1-b-continued

In the general formula (Ib):

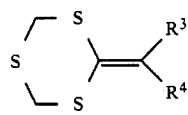

| Compound No. | $R^3$ | $R^4$ | Physical properties (melting point or refractive index) |
|---|---|---|---|
| 96 | ―〈benzene〉―O―〈benzene〉―F | $CH_3$ | m.p. 66.0–67.0° C. |
| 97 | ―〈benzene〉―O―〈benzene〉―F | $C_2H_5$ | m.p. 87.5–88.0° C. |
| 98 | ―〈benzene〉―O―〈benzene〉―F | $CH_3$ | Paste |
| 99 | ―〈benzene〉―O―〈benzene〉―$CH_3$ | $CH_3$ | m.p. 91.5–92.8° C. |
| 100 | ―〈benzene〉―O―〈benzene〉―$OCH_3$ | $CH_3$ | m.p. 54.5–55.5° C. |
| 101 | ―〈benzene〉―O―〈benzene〉 | ―$COOC_2H_5$ | m.p. 134.0–135.0° C. |
| 102 | ―〈benzene〉―O―〈benzene〉 | ―COOH | m.p. 106.0–107.0° C. |
| 103 | ―〈benzene〉―O―〈benzene〉 | ―$CH_2OCH_3$ | $n_D^{22}$ 1.6557 |
| 104 | ―〈benzene〉―O―〈benzene〉―F | ―$CH_2CH_2COOCH_3$ | Paste |
| 105 | ―〈benzene〉―O―〈benzene〉―F | ―$CH_2CH_2COOH$ | m.p. 110.5–115.0° C. |
| 106 | ―〈benzene〉―O―〈pyridine〉 | $CH_3$ | m.p. 102.0–105.0° C. |

TABLE 1-b-continued

In the general formula (Ib):

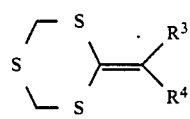

| Compound No. | R³ | R⁴ | Physical properties (melting point or refractive index) |
|---|---|---|---|
| 107 | 3-pyridyl | phenyl | m.p. 117.0–118.5° C. |
| 108 | 4-pyridyl | phenyl | m.p. 170.0–170.5° C. |
| 109 | 3-pyridyl | 4-F-phenyl | m.p. 117.0–119.0° C. |
| 110 | 2-furyl | 4-F-phenyl | m.p. 142.0–144.0° C. |
| 111 | 3,4-dimethyl-5-methyl-isoxazolyl | 4-F-phenyl | m.p. 80.0–81.0° C. |
| 112 | 2-thienyl | phenyl | m.p. 132.5–133.0° C. |
| 113 | 3,4-dimethyl-5-methyl-isoxazolyl | 4-CH₃-phenyl | m.p. 89.0–90.0° C. |
| 114 | 3-pyridyl | CH₃ | m.p. 69.0–70.0° C. |
| 115 | 4-F-phenyl | CH₃ | Paste |
| 116 | 2-thienyl | CH₃ | " |
| 117 | 2-naphthyl | CH₃ | m.p. 76.0–77.0° C. |

TABLE 1-b-continued
In the general formula (Ib):
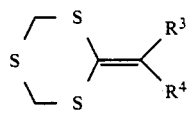
| Compound No. | R³ | R⁴ | Physical properties (melting point or refractive index) |
|---|---|---|---|
| 118 | (phenanthrenyl) | CH₃ | m.p. 96.0–97.0° C. |
| 119 | —CH₂N(phthalimide) | CH₃ | m.p. 164.0–165.5° C. |
| 120 | —CH₂CH₂N(phthalimide) | CH₃ | m.p. 139.0–140.5° C. |
| 121 | —CH₂—C₆H₄—O—C₆H₅ | CH₃ | $n_D^{22.0}$ 1.6627 |
| 122 | —CH=CH—C₆H₄—F | CH=CH—C₆H₄—F | m.p. 168.5–169.5° C. |
| 123 | —C₆H₄—O—C₆H₅ | CH₂OH | $n_D^{24.5}$ 1.6741 |
| 124 | —C₆H₄—O—C₆H₄—F | CH₃ | m.p. 93.5–95.0 |
| 125 | H | (CH₂)₆(CH₂CH=CH)₂—(CH₂)₄CH₃ (cis form) | $n_D^{18.5}$ 1.5465 |
| 126 | =fluorenylidene | | m.p. 208–210.0° C. |

TABLE 1-c

In the general formula (Ic):

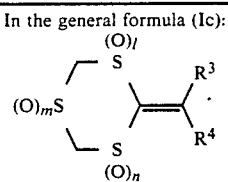

| Compound No. | n | m | l | R³ | R⁴ | Physical properties (melting point or refractive index) |
|---|---|---|---|---|---|---|
| 127 | 0 | 1 | 0 | C₆H₄-F | C₆H₅ | m.p. 156.0–158.5° C. |
| 128 | 0 | 1 | 0 | C₆H₄-F | C₆H₄-F | m.p. 155.0–156.5° C. |
| 129 | 0 | 1 | 1 | C₆H₄-F | C₆H₄-F | m.p. 171.0–173.0° C. |
| 130 | 0 | 2 | 0 | C₆H₄-F | C₆H₄-F | m.p. 163.0–166.0° C. |
| 131 | 0 | 1 | 0 | C₆H₄-O-C₆H₅ | CH₃ | m.p. 123.5–124.5° C. |
| 132 | 0 | 1 | 0 | C₆H₄-O-C₆H₅ | C₂H₅ | m.p. 103.5–105.5° C. |

Next, in Table 2 are shown NMR spectra data of the compounds whose physical properties are expressed in the term "paste".

TABLE 2

| Compound No. | NMR $_{TMS}{}^{CDCl_3}$ (ppm) |
|---|---|
| 16 | 0.76 (3H, t), 1.15–2.1 (2H, m) 2.6–3.05 (1H, m), 3.87 (2H, d) 4.3 (2H, d), 4.4 (1H, d) 6.7–7.4 (9H, m) |
| 19 | 1.45 (S, 6H), 3.95–4.40 (m, 4H) 5.95 (S, 1H), 7.03–7.20 (m, 4H) |
| 87 | 2.17 (3H, S), 3.95 (2H, S), 4.13 (2H, S) 6.75–7.6 (9H, m) |
| 91 | 0.85 (3H, t), 1.0–1.5 (4H, m), 2.6 (2H, t), 3.9 (2H, s), 4.1 (2H, S), 6.7–7.5 (9H, m) |
| 98 | 2.18 (3H, S), 3.93 (2H, S), 4.12 (S, 2H) 6.73–7.50 (8H, m) |
| 104 | 2.33 (2H, t), 3.00 (2H, t), 3.60 (3H, S) 3.97 (2H, S), 4.17 (2H, S), 6.87–7.33 (8H, m) |
| 115 | 2.20 (3H, S), 4.07 (2H, S), 4.17 (2H, S) 6.27–6.53 (2H, m), 7.23–7.40 (1H, m) |
| 116 | 2.27 (3H, S), 4.03 (2H, S), 4.13 (2H, S) 6.87–7.30 (3H, m) |

The 1,3,5-trithiane derivatives of the general formula (I) have such a low toxicity that even when said derivative is administered to a mouse or a rat at a does of 300 mg/kg/day for several consecutive days, the mouse or rat neither shows toxic symptoms nor dies.

The compounds of the general formula (I) are useful as drugs for curing arteriosclerosis and hyperlipemia. For example, it is known that hyperlipemia can be experimentally caused in a healthy test animal by giving thereto a feed containing a large amount of cholesterol, neutral fat, etc., and it was found that some of the compounds of the general formula (I) showed a marked cholesterol-reducing effect and a marked neutral-fat-reducing effect in the test animal suffering from experimentally caused hyperlipemia when administered orally or parenterally. Therefore, said compounds are useful as anti-hyperlipemic agents. Furthermore, by virtue of these pharmacological effects, said compounds are useful also in depressing arteriosclerosis caused by hyperlipemia and in preventing cerebral apoplexy and myocardial infarction.

Arteriosclerosis, in particular, atherosclerosis is caused by deposition of lipid on arterial wall which results in hyperplasia and sclerosis.

Arteriosclerosis obstructs blood flow and inhibits the supply of oxygen to tissues. Particularly in brain or heart, it is known as the so-called "isochemic pathosis", namely, a main dangerous factor of cerebral infaraction and myocardial infaraction. In addition, arteriosclerosis reduces the flexibility of artery and causes cerebral hemorrhage. Therefore, the blood lipd reducing effect of the compounds of this invention is effective also in depressing arteriosclerosis, and hence useful in preventing cerebral apoplexy.

Moreover, the compounds of this invention were found to have the effect of reducing cholesterol in blood by inhibition of cholesterol absorption in intestine and depression of cholesterol synthesis and promotion of cholesterol excretion in liver.

Accordingly, the term "drugs for curing hyperlipemia" used in the present specification means drugs for curing hyperlipemia and preventing and/or curing various diseases caused thereby, by utilizing the pharmacological effects described above.

The compounds of the general formula (I) can be used as they are as drugs for curing hyperlipemia and arteriosclerosis. It is also possible to formulate them into mixtures with pharmaceutically acceptable diluents and/or other pharmacologically active ingredients according to pharmaceutical custom. Furthermore, they can be formulated also into dosage unit forms. Forms which they can have as drugs include powder, granules, tablets, dragées, capsules, pills, suspensions, solutions, emulsions, ampuls, injections, isotonic solutions, etc.

Formulation of the compound of this invention into a medicinal composition includes an embodiment in which the compound of the general formula (I) is incorporated into the composition in the form of a mixture with pharmaceutically acceptable diluents. The term "diluents" used herein means materials other than the compound of the general formula (I). The diluents may be any of solids, semisolids, liquids and ingestable capsules and include various materials, for example, excipients, extenders, binders, wetting agents, disintegrators, surfactants, lubricants, dispersants, buffers, taste-improver, odour-reducing agents, coloring matters, perfumes, preservatives, dissolution assistance, solvents, coatings, frostings, etc. But the diluents are not limited thereto. These materials are used alone or as a mixture thereof. Such pharmaceutically acceptable diluents are used as a mixture with other pharmacologically active ingredients in some cases.

A medicinal composition using the compound of this invention may be produced by any known method. For example, the active ingredient is mixed with pharmaceutically acceptable diluents to yield, for instance, granules, and then the composition thus obtained is formed, for example, into tablets. When the medicinal composition is used as a parenteral drugs, it should be sterilized. If necessary, it should be made isotonic with regard to blood.

In this invention, since the compounds of the above general formula (I) themselves are applicable as drugs for curing hyperlipemia and arteriosclerosis, the active ingredient is contained in the composition usually in an amount of 0.01 to 100% by weight.

When the compound of this invention is formulated into a preparation of dosage unit, individual pharmaceutical portions constituting said preparation may be either in different forms or in the same forms, and there are often employed, for example, forms such as tablets, granules, pills, powder, dragées, capsules, and ampuls.

The drugs for curing hyperlipemia and arteriosclerosis according to this invention can be applied to human beings and animals in order to prevent and cure hyperlipemia and arteriosclerosis, by a method which is conventional in the fields of such prevention and curing treatment. They are administered orally or parenterally. The oral administration includes sublingual administration. The parenteral administration includes administration by injection (including, for example, subcutaneous injection, intramuscular injection, intravenous injection, and drip).

The dose of the drugs of this invention is varied depending on various factors such as the species of subject (animals or human beings), its sensitivity, age, sex and body weight, the administration route, time and internal of administration, the condition of a disease, the physical condition of the subject, the properties of pharmaceutical preparation, the kind of proparation, the kind of active ingredient, etc.

Therefore, in some cases, a dose smaller than the minimum dose described below is sufficient, and in other cases, a dose larger than the maximum dose described below is required.

In the case of a high dose, administration in several times a day is preferred.

In order to obtain effective results for animals, the dose in terms of the active ingredient is advantageously 0.1 to 500 mg, preferably 0.1 to 30 mg per kg of body weight per day in the case of oral administration, while in the case of parenteral administration, it is advantageously 0.01 to 250 mg, preferably 0.1 to 25 mg per kg of body weight per day.

In order to obtain effective results for human beings, in consideration of sensitivity difference, safety, etc. on the basis of the effective dose for animals, the dose for human beings seems to be advantageously, for example, in the following ranges: in the case of oral administration, 0.1 to 200 mg, preferably 0.5 to 50 mg per kg of body weight per day, and in the case of parenteral administration, 0.01 to 100 mg, preferably 0.1 to 25 mg per kg of body weight per day.

Next, Examples of the 1,3,5-trithiane derivatives of this invention are described below.

EXAMPLE 1

2-{Bis(4-fluorophenyl)hydroxymethyl}-1,3,5-trithiane (compound No. 7)

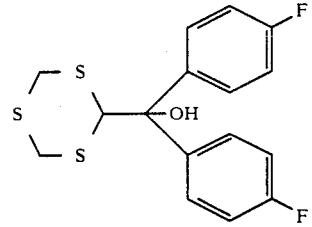

In 30 ml of anhydrous tetrahydrofuran was suspended 2.6 g of 1,3,5-trithiane, and 12 ml of 1.6M n-bytyl lithium was added dropwise under an argon atmosphere at a temperature of about $-20°$ C. After completion of the dropwise addition, the resulting mixture was stirred for 2 hours. Next, the reaction mixture was cooled to about $-60°$ C., and then a solution of 4.4 g of 4,4'-difluorobenzophenone dissolved in 100 ml of tetrahydrofuran was dropped thereinto. After completion of the dropping, the reaction temperature was slowly raised to $0°$ C. After stirring at $0°$ C. for another 1 hour, the reaction mixture thus obtained was poured into ice water and the resulting mixture was extracted with chloroform. The extract was washed with a saturated aqueous sodium chloride solution and then dried over anhydrous magnesium sulfate, and the solvent was removed by distillation under reduced pressure. The crude product thus obtained was recrystallized from ether-hexane to give 5.58 g of the desired compound.

Yield 81.5%, m.p. 124.0°–125° C.

EXAMPLE 2

2-{(2,5-Dimethylisoxazol-4-yl)(4-tolyl)hydroxymethyl}-1,3,5-trithiane (compound No. 14)

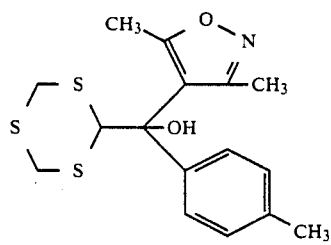

In 25 ml of anhydrous tetrahydrofuran was suspended 1.9 g of 1,3,5-trithiane, and 9 ml of 1.6M n-butyl lithium was added dropwise under an argon atmosphere at a temperature of about −20° C. After completion of the dropwise addition, the resulting mixture was stirred for 2 hours. Next, the reaction mixture was cooled to about −60° C., and then a solution of 3.0 g of 5,4-(4-methylbenzoyl)-2,5-dimethylisoxazole dissolved in 10 ml of tetrahydrofuran was dropped thereinto. After completion of the dropping, the reaction temperature was slowly raised to 0° C. The mixture thus obtained was stirred at 0° C. for another 1 hour. Thereafter, the same treatment as in Example 1 was carried out to obtain a crude product, which was then purified by a silica gel column chromatography (chloroform) to give 3.4 g of the desired compound.

Yield 70.0%, m.p. 150.5°–151.5° C.

EXAMPLE 3

2-{1-(4-Phenoxyphenyl)-1-hydroxyethan-1-yl}-1,3,5-trithiane (compound No. 17)

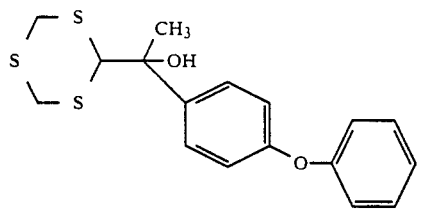

In 30 ml of anhydrous tetrahydrofuran was suspended 2.6 g of 1,3,5-trithiane, and 12 ml of 1.6M n-butyl lithium was added dropwise under an argon atmosphere at a temperature of about −20° C. After completion of the dropwise addition, the resulting mixture was stirred for 2 hours. Next, the reaction mixture was cooled to about −60° C., and then a solution of 4.0 g of 4-phenoxyacetophenone dissolved in 10 ml of tetrahydrofuran was dropped thereinto. After completion of the dropping, the reaction temperature was slowly raised to 0° C. The mixture thus obtained was stirred at 0° C. for another 1 hour. Thereafter, the same treatment as in Example 1 was carried out to obtain a crude product, which was then purified by a silica gel column chromatography (chloroform) to give 3.4 g of the desired compound.

Yield 70.0%, m.p. 70.0°–71.0° C.

EXAMPLE 4

2-(4,4′-difluorobenzhydrylidene)-1,3,5-trithiane (compound No. 33)

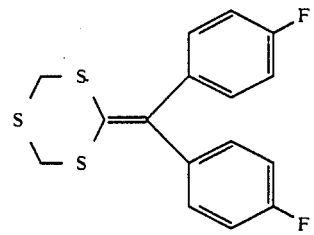

A mixture of 2.0 g of 2-{bis(4-fluorophenyl)hydroxymethyl}-1,3,5-trithiane, 0.2 g of p-toluenesulfonic acid and 50 ml of benzene was refluxed with heating for 15 minutes by means of a Dean-Stark reflux condenser. After being cooled, the mixture was extracted with ethyl acetate and the extract was washed with a saturated aqueous sodium hydrogencarbonate solution. The washed extract was dried over anhydrous magnesium sulfate and the solvent was removed by distillation under reduced pressure to obtain a material, which was recrystalized from cyclohexane to give 1.7 g of the desired compound.

Yield 80.7%, m.p. 153.0°–153.5° C.

EXAMPLE 5

2-{(2,5-Dimethylisoxazol-4-yl)(4-tolyl)methylene}-1,3,5-trithiane (compound No. 113)

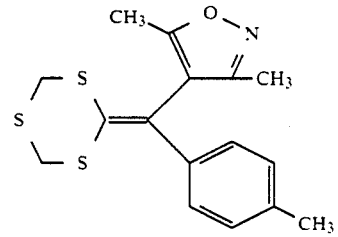

In the same manner as in Example 4, 2.0 g of 2-{(2,5-dimethylisoxazol-4-yl)(4-tolyl)methylol}-1,3,5-trithiane was treated. The crude product thus obtained was purified by a silica gel column chromatography (chloroform:hexane=3:1) to give 1.7 g of the desired compound.

Yield 89.6%, m.p. 89.0°–90.0° C.

EXAMPLE 6

2-{(4-Phenoxyphenyl)(ethoxycarbonyl)methylene}-1,3,5-trithiane (compound No. 101)

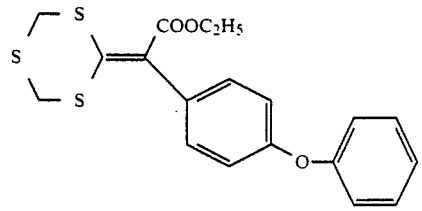

In 50 ml of anhydrous tetrahydrofuran was dissolved 1.58 g of 2-dimethylphosphoryl-1,3,5-trithiane, and 4 ml of 1.6M n-butyl lithium was added dropwise under an argon atmosphere at a temperature of about −70° C. After completion of the dropwise addition, the resulting mixture was stirred for 1 hour. Next, a solution of 1.41 g of ethyl 4-phenoxypheny191yoxylate dissolved in 5 ml of tetrahydrofuran was dropped thereinto. After completion of the dropping, the reaction temperature was slowly raised to room temperature and the mixture thus obtained was stirred overnight. Thereafter, the same treatment as in Example 1 was carried out to give a crude product, which was then purified by a silica gel column chromatography (chloroform:hexane=2:1) to obtain 1.63 g of the desired compound.

Yield 77.0%, m.p. 134.0°–135.0° C.

EXAMPLE 7

2-[1-{4-(3-morpholinopropyloxy)phenyl}ethane-1-ylidene]-1,3,5-trithiane (compound No. 83)

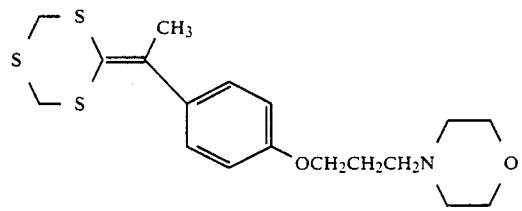

In anhydrous tetrahydrofuran was dissolved 3.0 g of 2-diethylphosphoryl-1,3,5-trithiane, and 7 ml of 1.6M n-butyl lithium was added dropwise under an argon atmosphere at a temperature of about −70° C. After completion of the dropwise addition, the resulting mixture was stirred for 1 hour. Next, a solution of 2.63 g of 4-(3-morpholinopropyloxy)acetophenone dissolved in 5 ml of tetrahydrofuran was dropped thereinto. After completion of the dropping, the reaction temperature was slowly raised to room temperature, and the mixture thus obtained was stirred overnight. Thereafter, the same treatment as in Example 1 was carried out to give a crude product, which was then purified by a silica gel column chromatography (chloroform:methanol=50:1) to give 3.3 g of the desired compound.

Yield 86.2%, m.p. 95.0°–98.0° C.

EXAMPLE 8

2-(1-Phenyl-9,12-cis,cis-octadecan-1-ylidene)-1,3,5-trithiane (compound No. 76)

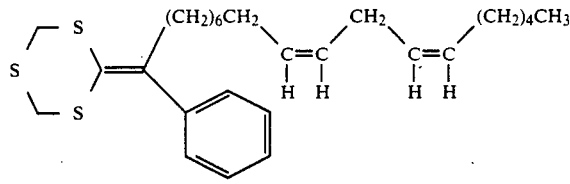

In 10 ml of anhydrous tetrahydrofuran was dissolved 1.1 g of 2-diethylphosphoryl-1,3,5-trithiane, and 2.5 ml of 1.6M n-butyl lithium was added dropwise under an argon atmosphere at −70° C. After completion of the dropwise addition, the resulting mixture was stirred for 1 hour. Next, a solution of 1.0 g of linoleylbenzene dissolved in 5 ml of tetrahydrofuran was dropped thereinto. After completion of the dropping, the reaction temperature was slowly raised to room temperature, and the mixture thus obtained was stirred overnight. Thereafter, the same treatment as in Example 1 was carried out to give a crude product, which was then purified by a silica gel column chromatography (chloroform:hexane=2:3) to give 1.1 g of the desired compound.

Yield 81.4%, $n^{18.5}_D$ 1.5709.

EXAMPLE 9

2-{1-(4-Phenoxyphenyl)propan-1-yl}-1,3,5-trithiane (compound No. 16)

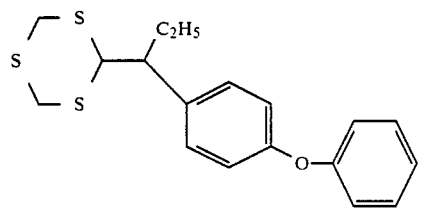

In 10 ml of anhydrous dichloromethane were dissolved 1.0 g of 2-{1-(4-phenoxyphenyl)propan-1-ylidene}-1,3,5-trithiane and 0.67 g of triethylsilane, and a solution prepared by diluting 1 ml of trifluoroacetic acid with 5 ml of dichloromethane was added dropwise at room temperature. The resulting solution was stirred overnight. After sodium carbonate powder was added, the resulting mixture was washed with water and dried over anhydrous sodium sulfate. The solvent was removed by distillation, and then the residue was purified by a silica gel column chromatography (chloroform:hexane=2:1) to give 0.91 g of the desired compound.

Yield 90.5%. paste.

EXAMPLE 10

2-{Bis(4-fluorophenyl)methyl}-1,3,5-trithane (compound No. 6)

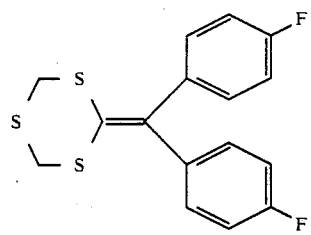

In 10 ml of anhydrous dichloromethane were dissolved 1.6 g of 2-{bis(4-fluorophenyl)hydroxymethyl}-1,3,5-trithiane and 0.68 g of triethylsilane, and a solution prepared by diluting 1 ml of trifluoroacetic acid with 5 ml of dichloromethane was added dropwise at room temperature. The resulting solution was stirred overnight. Thereafter, the same treatment as in Example 9 was carried out, and 0.83 g of the desired compound was obtained.

Yield 54.0%, m.p. 170.0°–171.0° C.

EXAMPLE 11

2-{Bis(4-fluorophenyl)}-2-imidazolylmethyl-1,3,5-trithiane (compound No. 8)

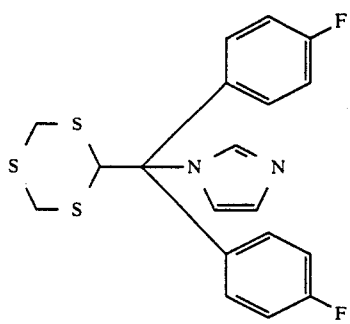

In 50 ml of methylene chloride were dissolved 2.48 g of 2-}Bis(4-fluorophenyl)hydroxymethyl}-1,3,5-trithiane and 2.53 g of imidazole, and a solution prepared by diluting 1.0 g of thionyl chloride with 5 ml of methylene chloride was added dropwise with ice-cooling. After completion of the dropwise addition, the resulting solution was stirred at the same temperature for 15 minutes and then at room temperature for 10 minutes. Subsequently, the reaction mixture was poured into 100 ml of water and was extracted with ethyl acetate, after which the extract was washed with water and dried over anhydrous sodium sulfate. The solvent was removed by distillation, and then the residue was purified by a silica gel column chromatography (chloroform:methanol=50:1) to give 1.24 g of the desired compound.

Yield 46.0%, m.p. 93.5°–96.0° C.

EXAMPLE 12

2-(4,4'-difluorobenzhydrylidene)-1,3,5-trithiane-5-oxide (compound No. 128)

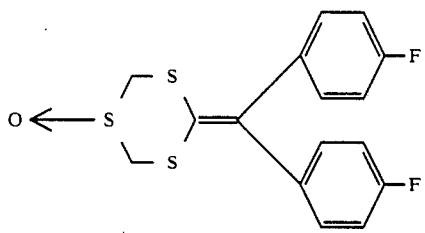

To a 30 ml of dichloromethane of 1.5 g of 2-(4,4'-difluorobenzhydrylidene)-1,3,5-trithiane was added 0.77 g of m-chloroperbenzoic acid in small portions at 0° C., and the resulting mixture was stirred overnight. After completion of the reaction, the reaction mixture was poured into ice-water and extracted with dichloromethane. Usual work up gave crude solid, which was purified by a silica gel column chromatography (chloroform:hexane=3:1) to obtain 1.2 g of white crystals.

Yield 76.4%, m.p. 155.0°–156.5° C.

In the following Examples, all parts are by weight. The kinds and proportions of ingredients can be widely varied.

EXAMPLE 13

A powder or fine granular preparation was prepared by mixing uniformly and pulverizing or granulating finely the following ingredients:
Compound 11: 10 parts
Ground magnesium oxide: 10 parts
Lactose: 80 parts

EXAMPLE 14

A powder was prepared according to Example 13 by using the following ingredient:
Compound 33: 10 parts
Synthetic aluminum silicate: 10 parts
Calcium hydrogenphosphate: 5 parts
Lactose: 75 parts

EXAMPLE 15

Granules were prepared by kneading together uniformly, grinding, granulating the following ingredients, drying the resultant, and then sieving:
Compound 82: 50 parts
Starch: 10 parts
Lactose: 15 parts
Crystalline cellulose: 20 parts
Polyvinyl alcohol: 5 parts
Water: 30 parts

EXAMPLE 16

Tablets having a diameter of 10 mm were prepared by mixing 99 parts of the granules obtained in Example 15 with 1 part of calcium stearate, and compression-molding the resulting mixture.

EXAMPLE 17

Granules were prepared in the same manner as in Example 15 except for using the following ingredients:
Compound 88: 78 parts
Polyvinyl alcohol: 2 parts
Lactose: 20 parts
Water: 30 parts
To 90 parts of the granules obtained was added 10 parts of crystalline cellulose, and the resulting mixture was compression-molded into tablets having a diameter of 8 mm. Then, the tablets were made into dragees by use of suitable amounts of a mixed suspension of syrup, gelatin and precipitated calcium carbonate and a coloring matter.

EXAMPLE 18

An injection was prepared by mixing by heating, and then sterilizing the following ingredients:
Compound 126: 0.5 part
Nonionic surface active agent: 2.5 parts
Physiological saline: 97 parts

EXAMPLE 19

Capsules were prepared by packing the powder obtained in Example 14 into commercially available capsular containers.

Next, test examples of the compounds of this invention are shown below.

TEST EXAMPLE 1 (Plasma lipid reducing effect (in mouse))

Test method: A high-cholesterol diet (HCD) was given to 6-day-old male mice for 7 days, and each compound to be tested was orally administered thereto every day at a dose of 100 and 300 mg/kg/day. Normal diet was given to a control group and a solvent used for administering the compounds to be treated was orally administered thereto alone. After completion of the feeding of high-cholesterol diet, blood was collected from the mice and plasma was separated from the blood. The plasma total cholesterol concentration (p-TC) was measured by a modified Zak-Henly method, and the cholesterol-reducing effect of the compound to be tested was calculated by the following equation and evaluated as p-TC reduction percentage:

$$\text{p-TC reduction percentage} = \frac{TC_{HCD} - TC_{treated}}{TC_{HCD} - TC_{cont.}} \times 100$$

wherein $TC_{HCD}$, $TC_{treated}$, and $TC_{cont.}$ have the following meanings:

$TC_{HCD}$: The total cholesterol concentration of the group to which a high cholesterol diet was given.

$TC_{treated}$: The total cholesterol concentration of the group to which each compound of this invention was administered.

$TC_{cont.}$: The total cholesterol concentration of the control group.

The results obtained are shown in Table 3.

TABLE 3

| Compound No. | Cholesterol reduction percentage (%) 100 mg/kg | Cholesterol reduction percentage (%) 300 mg/kg | Compound No. | Cholesterol reduction percentage (%) 100 mg/kg | Cholesterol reduction percentage (%) 300 mg/kg |
|---|---|---|---|---|---|
| 2 |  | 34.3 | 61 |  | 61.9 |
| 3 |  | 26.4 | 64 |  | 30.4 |
| 11 | 54.8 | 52.2 | 68 |  | 119.4 |
| 22 | 24.8 |  | 69 |  | 81.0 |
| 24 | 82.4 | 91.9 | 76 |  | 49.7 |
| 26 | 62.0 |  | 85 |  | 4.6 |
| 27 | 55.0 | 50.5 | 89 | 74.6 |  |
| 31 |  | 39.9 | 90 | 12.4 |  |
| 33 | 49.2 | 92.7 | 96 |  | 64.2 |
| 35 |  | 80.1 | 98 |  | 14.0 |
| 36 | 76.3 | 60.1 | 104 |  | 53.8 |
| 39 |  | 4.6 | 105 |  | 40.4 |
| 44 | 41.9 | 133.1 | 107 | 16.1 |  |
| 45 | 25.7 |  | 108 |  | 202.6 |
| 46 | 56.3 |  | 110 |  | 6.4 |
| 47 | 35.8 | 45.3 | 114 | 17.7 |  |
| 48 |  | 87.9 | 117 |  | 129.6 |
| 49 |  | 68.6 | 119 |  | 51.4 |
| 51 |  | 30.5 | 129 |  | 62.3 |
| 53 | 52.6 |  | 130 | 84.3 | 165.3 |
| 55 | 40.6 |  | Reference compound A | 0 | 0 |
| 56 |  | 106.8 |  |  |  |
| 59 | 66.2 |  | Reference | 0 | 0 |

TABLE 3-continued

| Compound No. | Cholesterol reduction percentage (%) 100 mg/kg | Cholesterol reduction percentage (%) 300 mg/kg | Compound No. | Cholesterol reduction percentage (%) 100 mg/kg | Cholesterol reduction percentage (%) 300 mg/kg |
|---|---|---|---|---|---|
|  |  |  | compound B |  |  |

Note:

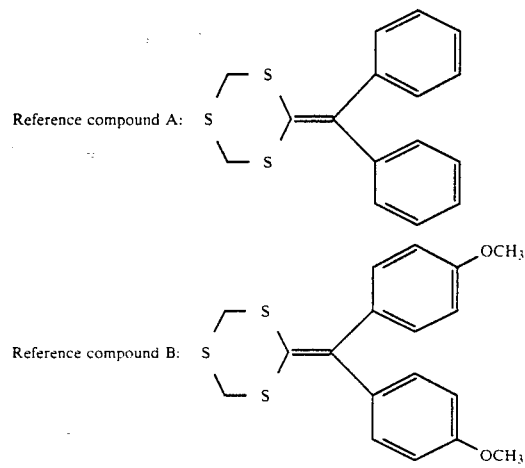

TEST EXAMPLE 2 (Serum lipid reducing effect (in rat))

Test method: A high-cholesterol diet (HCD) was given the 4-week-old male Wistar strain rats for 7 days. On the fourth day after the beginning of this feeding, blood was drawn from the plexus venosus in eyeground by means of a capillary tube (heparin-treated, 75 mm, Drummond Scientific) without fasting, and plasma was separated from the blood. The plasma total cholesterol concentration (p-TC) before the beginning of administration of a compound to be treated was measured, and the animals were divided into groups so as to minimize the scatter of p-TC values in each group. Each compound to be treated and a reference compound were individually suspended in a 2% (W/V) aqueous gum arabic solution in a concentrating of 0.2 or 0.6%, or 0.6 or 6.0% (W/V), and each of the suspension thus prepared was administered every day in an amount of 5 ml/kg/day for the latter 4 days of the above 7 days. Powdery feed was orally administered to a control group of 7 days, a 2% aqueous gum arabic solution was similarly administered thereto for the latter 4 days of these 7 days. After fasting for 16 hours from 8 hours after the last administration of the compound to be tested, blood was drawn from the carotid artery under ether anesthesia and serum was separated from the blood and analyzed for lipid. The serum total cholesterol concentration (p-TC) was measured by a modified Zac-Henly method, and the cholesterol reducing effect of the compound to be tested was calculated by the following equation and evaluated as TC reduction percentage:

$$\text{TC reduction percentage (\%)} = \frac{TC_b - TC_c}{TC_b - TC_a} \times 100$$

wherein $TC_a$ = the total cholesterol concentration of the control group.

$TC_b$ = the total cholesterol concentration of the group to which a high-cholesterol diet was given.

$TC_c$ = the total cholesterol concentration of the group to which each compound of this invention is administered.

The results obtained are shown in Table 4.

TABLE 4

| Compound No. | Cholesterol reduction percentage (%) | | Compound No. | Cholesterol reduction percentage (%) | |
|---|---|---|---|---|---|
| | 10 mg/kg | 30 mg/kg | | 10 mg/kg | 30 mg/kg |
| 6 | 24 | 46 | 89 | 34 | 62 |
| 11 | 25 | 51 | 96 | 48 | 60 |
| 16 | 17 | 40 | 104 | 38 | 39 |
| 17 | 29 | 19 | 105 | 34 | 43 |
| 31 | 29 | 52 | 107 | 12 | 31 |
| 33 | 56 | 84 | 110 | 27 | 30 |
| 34 | −8 | 27 | 126 | 38 | 42 |
| 35 | 24 | 19 | 129 | −14 | 42 |
| 42 | 40 | 14 | 130 | 44 | 57 |
| 63 | 32 | 64 | Reference compound C | 30 mg/kg | 300 mg/kg |
| 82 | 49 | 51 | | | |
| 88 | −16 | 42 | | −60 | 73 |

Note:

Reference compound C: 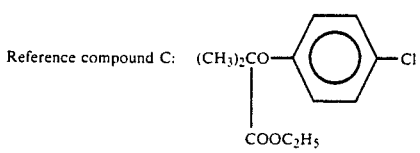

As shown in Table 3 and Table 4, the compounds of this invention show a cholesterol-reducing effect and have an anti-hyperlipemic activity.

What is claimed is:

1. A 1,3,5-trithiane derivative represented by the formula (I):

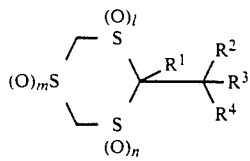 (I)

wherein in the formula (I), $R^1$ and $R^2$ in combination with each other, form a double bond between the carbon atom of the trithiane ring and the one to which $R^3$ and $R^4$ are bonded, wherein $R^3$ is a substituted phenyl group having as the substituent a phenoxy group (which is optionally substituted by one or two substituents selected from the group consisting of halogen atoms, $C_1$- to $C_5$- alkyl groups and $C_1$- to $C_5$-alkoxy groups), and $R^4$ is a $C_1$- to $C_8$-alkyl group (which is optionally substituted by a $C_2$- to $C_5$-alkoxycarbonyl group or a $C_1$- to $C_5$-alkoxy group), and each of l, m and n is zero or an integer of 1 or 2.

2. A 1,3,5-trithiane derivative represented by the formula (I):

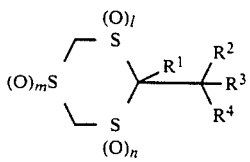 (I)

wherein $R^1$ and $R^2$ in combination with each other, form a double bond between the carbon atom of the trithiane derivative and the one to which $R^3$ and $R^4$ are bonded, $R^3$ is a halophenyl group or a phenoxyphenyl group, and $R^4$ is a $C_1$- to $C_5$-alkyl group, and each of l, m and n is zero or an integer of 1 to 2.

3. A compound according to claim 1, wherein the trithiane derivative is 2-{1-(4-phenoxphenyl)propan-1-ylidene}-1,3,5-trithiane.

4. A compound according to claim 1, wherein the trithiane derivative is 2-{1-(4-phenoxyphenyl)ethan-1-ylidene}-1,3,5-trithiane.

5. A compound according to claim 1, wherein the trithiane derivative is 2-[{1-(4-phenoxyphenyl)-2-methoxy}-ethan-1-ylidene]-1,3,5-trithiane.

6. A compound according to claim 1, wherein the trithiane derivative is 2-[1-{4-(4-fluorophenoxy)-phenyl}propan-1-ylidene]-1,3,5-trithiane.

7. A 1,3,5-trithiane derivative which is 2-[{4-(2-etoxycarbonyl-propan-2-oxyphenyl}ethan -1-ylidene]-1,3,5-trithiane.

8. A compound according to claim 1, wherein the trithiane derivative is 2-{1-(4-phenoxyphenyl)ethan-1-ylidene}-1,3,5-trithiane-5-oxide.

9. A compound according to claim 1, wherein the trithiane derivative is 2-{1-(4-phenoxyphenyl) propan-1-ylidene} -1,3,5-trithiane-5-oxide.

10. A medicinal composition comprising a pharmaceutically acceptable carrier and as active ingredient a trithiane derivative represented by the formula (I):

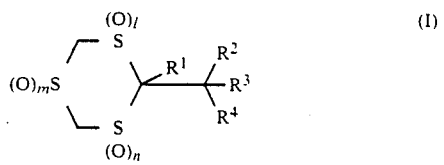 (I)

wherein $R^2$, when taken together with $R^1$, forms a double bond between the carbon atom of the trithiane ring and the one to which $R^3$ and $R^4$ are bonded, and each of l, m and n is zero, and
wherein in formula (I) $R^3$ is a substituted phenyl group having as the substituent a phenoxy group (which is optionally substituted by one or two substituents selected from the group consisting of halogen atoms, $C_1$- to $C_5$-alkyl groups and $C_1$- to $C_5$-alkoxy groups), and $R^4$ is selected from the group consisting of a $C_1$- to $C_5$-alkyl group and a hydroxycarbonyl $C_1$- to $C_5$-alkyl group.

11. A medicinal composition comprising a pharmaceutically acceptable carrier and as active ingredient a trithiane derivative represented by the formula (I):

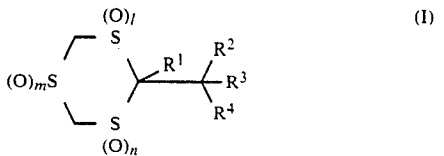 (I)

wherein $R^2$, when taken together with $R^1$, forms a double bond between the carbon atom of the trithiane ring and the one to which $R^3$ and $R^4$ are bonded, and each of l, m and n is zero or an integer of 1 or 2, and
wherein in formula (I) $R^3$ is a holophenyl group or a phenoxyphenyl group, and $R^4$ is a $C_1$- to $C_5$-alkyl group.

12. A medicinal composition comprising 2-{1-(4-phenoxyphenyl) propan-1-ylidene}-1,3,5-trithiane and a pharmaceutically acceptable carrier.

13. A medicinal composition comprising 2-{1-(4-phenoxyphenyl) ethan-1-ylidene}-1,3,5-tritiane and a pharmaceutically acceptable carrier.

14. A medicinal composition comprising 2-[{1-(4-phenoxyphenyl) -2-methoxy}ethan-1-ylidene]-1,3,5-trithiane and a pharmaceutically acceptable carrier.

15. A medicinal composition comprising 2-[1-{4-(4-fluorophenoxy) phenyl} propane-1-ylidene]-1,3,5-trithiane and a pharmaceutically acceptable carrier.

16. A medicinal composition comprising 2-[1-{4(2-ethoxycarbonyl-propane-2-oxy) phenyl} ethane-1-ylidene]-1,3,5-trithiane and a pharmaceutically acceptable carrier.

17. A medicinal composition comprising 2-{1-(4-phenoxyphenyl) ethane-1-ylidene}-1,3,5-trithiane-5-oxide and a pharmaceutically acceptable carrier.

18. A medicinal composition comprising 2-}1-(4-phenoxyphenyl) propan-1-ylidene}-1,3,5-trithiane-5-oxide and a pharmaceutically acceptable carrier.

* * * * *